(12) United States Patent
Warner et al.

(10) Patent No.: US 7,612,232 B2
(45) Date of Patent: Nov. 3, 2009

(54) PURIFICATION OF ACETIC ACID FROM WOOD ACETYLATION PROCESS

(75) Inventors: R. Jay Warner, Houston, TX (US); Melchior A. Meilchen, Houston, TX (US); Michael O. Streb, Hünfelden/Ohren (DE); Nathan K. Powell, Waxahachie, TX (US); Rolf Soellner, Hofheim (DE)

(73) Assignee: Celanese International Corporation, Dallas, TX (US)

( * ) Notice: Subject to any disclaimer, the term of this patent is extended or adjusted under 35 U.S.C. 154(b) by 0 days.

(21) Appl. No.: 12/079,452

(22) Filed: Mar. 27, 2008

(65) Prior Publication Data

US 2009/0247788 A1 Oct. 1, 2009

(51) Int. Cl.
*C07C 51/42* (2006.01)
(52) U.S. Cl. ...................................................... 562/608
(58) Field of Classification Search ........................ None
See application file for complete search history.

(56) References Cited

U.S. PATENT DOCUMENTS 3,024,170 A    3/1962  Othmer et al.
4,804,384 A *  2/1989  Rowell et al. .................. 8/121
5,160,412 A   11/1992  Berg
7,355,066 B1 * 4/2008  Johnson et al. ............. 560/239

FOREIGN PATENT DOCUMENTS

EP    0 213 252 A1    3/1987
EP    0680810    * 11/1995

OTHER PUBLICATIONS

International Search Report and Written Opinion.

* cited by examiner

*Primary Examiner*—Karl J Puttlitz
(74) *Attorney, Agent, or Firm*—Michael W. Ferrell (57) ABSTRACT

A method of purifying acetic acid containing terpene and terpenoid impurities, includes: (a) supplying acetic acid containing terpene or terpenoid impurities and water to a distillation column; (b) azeotropically removing terpene or terpenoid impurities from the mixture of acetic acid and water supplied to the column as distillate; and (c) withdrawing a product stream from the column comprising acetic acid purified of terpene or terpenoid impurities. The method is particularly effective for purifying acetic acid recovered from a wood purification process.

29 Claims, 4 Drawing Sheets

PURIFICATION OF ACETIC ACID FROM WOOD ACETYLATION PROCESS

FIELD OF INVENTION

The present invention relates to purification of acetic acid recovered from a wood acetylation process, and in particular, to removal of terpene and terpenoid impurities from the acid.

BACKGROUND OF THE INVENTION

Acetylation of wood improves its resistance to degradation. Commercial processes include variants of the process disclosed in WO 2005/077626 A1 of New Zealand Forest Research Institute Limited. See, also, United States Publication No. 2004/0258941 to Neogi et al., United States Publication No. 2007/0128422 A1 of Nasheri et al., EP 0213252 A1 of Rowell et al., U.S. Pat. No. 5,525,721 to Ohshima et al., and EP 0680810 A1 of Stichting Hout Research for similar and related disclosure.

Generally speaking, the wood acetylation process noted above includes the steps of contacting wood with acetic anhydride to acetylate the cellulose to provide rot and termite resistance. During this process, a byproduct stream including an acetic anhydride/acetic acid mixture is generated. The acetic anhydride is separated from the acid and recycled back to the acetylation step, while the spent acetic acid must be purified before it is used in other products and/or reprocessed into acetic anhydride by way of ketene reaction, for example. If the spent acetic acid is not purified, final product quality will be impacted.

Recovery and separation of an acetic anhydride/acetic acid mixture after completion of a wood acetylation step is known in the art. In EP 0213252 A1 and EP 0680810 A1 (discussed above) it is noted that the acid can be purified by way of fractional distillation. Acid purification by distillation is also disclosed in US 2004/0258941 (discussed above), and JP 56008016 B of Daicel Chemical Industries, Ltd. See, also, U.S. Pat. No. 3,496,159 to Spence for fractional distillation of acids generally.

In EP 686619 of Commissariat a L'Energie Atomique, it is noted that organic impurities can be removed from condensed acetic acid vapor recovered from a distillation column by way of extraction.

While the foregoing methods are no doubt effective to somewhat purify the recovered acetic acid, it has been found that terpenes and terpenoid impurities, especially high boiling-point compounds, are difficult to remove and present a challenging technical obstacle to reuse of the recovered acetic acid in applications requiring high purity product. The problem is particularly difficult with "dry" acetic acid since terpene and terpenoid impurities are soluble in concentrated or glacial acetic acid.

SUMMARY OF THE INVENTION

It has been unexpectedly found that anhydrous acetic acid recovered from a wood acetylation process of the class described in WO 05/077626 A1 can be efficiently purified by way of azeotropic distillation with water. For example, the acetic acid is purified by feeding acetic acid and water to a distillation column; azeotropically removing terpene or terpenoid impurities from the mixture of acetic acid and water supplied to the column as distillate; and withdrawing a typically liquid product stream from the column comprising acetic acid purified of terpene or terpenoid impurities. The process of invention is particularly surprising in view of the fact that conventional fractional distillation of the dry acid does not remove the following impurities efficiently:

Furthermore, these impurities are not very soluble in water, yet we have found that they advantageously form azeotropes with water and are readily removed by azeotropic distillation.

Other aspects and advantages of the present invention are described in the detailed description below and in the claims.

BRIEF DESCRIPTION OF THE DRAWINGS

The invention is described in detail below with reference to the appended drawings, wherein like numerals designate similar parts. In the Figures.

DETAILED DESCRIPTION OF THE INVENTION

The invention is described in detail below with reference to several embodiments and numerous examples. Such discussion is for purposes of illustration only. Modifications to particular examples within the spirit and scope of the present invention, set forth in the appended claims, will be readily apparent to one of skill in the art. Terminology used herein is given its ordinary meaning consistent with the exemplary definitions set forth immediately below. Percentages, ppm, ratios and so forth are on a weight basis unless otherwise specified.

The term "glacial acetic acid" as used herein refers to acetic acid that contains less than about 0.2 weight % water. Typical specification limits for a sales-grade glacial acetic acid product include a minimum assay of 99.85 wt %, a maximum water content of 0.15 wt %, a maximum color of 10, as well as a minimum permanganate time of 2 hours.

The term "organic impurities" as used herein refers to a variety of impurities contained in acetic acid recovered from the acetylation process. Such impurities may include terpinenes, terpinolenes, α-terpineol acetate, α-terpineol, α-pinene, α-fenchene, camphene, p-methyl isopropyl benzene (p-cymene), limonenes, α-fenchyl acetate, isobornyl acetate, pinocarvyl acetate, acetaldehyde, acetone, acetonitrile, methyl acetate, ethyl acetate, methoxy acetic acid, and propionic acid.

The term "light-ends" as used herein refers to a number of impurities present in recovered acetic acid that have boiling points lower than that of acetic acid. These compounds include those identified below along with their chemical structures.

ethyl acetate (B.P. 77° C.)

acetaldehyde (B.P. 20.2° C.)

acetone (B.P. 56.2° C.)

methyl acetate (B.P. 54.05° C.)

The term "terpene and terpenoid impurities" as used herein refers to impurities found in recovered acetic acid used in the process disclosed in WO 2005/077626 A1. Terpenes are derivatives of isoprene, can be acyclic, monocyclic, bicyclic, or tricyclic, and are generally unsaturated. Terpenoids are saturated isomers and derivatives of terpenes, such as alcohols, aldehydes, and esters. These impurities include the compounds identified below, along with their chemical structures. Note that different isomers are sometimes simply referred to by their generic names herein. Note, also, reference to one genus or class of compounds in plural form contemplates reference to isomers or members within the genus or class.

α-pinene

β-pinene camphene limonene 1-isopropyl-4-methyl-cyclohexa-1,4-diene terpinene 1-methyl-4-(1-methylethylidene)-cyclohexene terpinolene 1-isopropyl-4-methylcyclohexa-1,3-diene terpinene α-fenchyl acetate 2-(4-methylcyclohex-3-enyl)-propan-2-ol α-terpineol isobornyl acetate 2-(4-methyl-3-cyclohexenyl)-2-propyl acetate terpineol acetate p-methyl isopropyl benzene Acetic acid recovered from a wood acetylation process exhibited poor permanganate times. Recovered acetic acid needs to be purified for end uses requiring a high grade acid product.

Fractional distillation of dry acid was investigated as a possible mode for removing terpene and terpenoid impurities. Exploratory investigations of purifying recovered acetic acid from a wood acetylation process—using batch distillation tests—showed that conventional fractional distillation was not particularly effective in removing the terpene and terpenoid impurities discussed above.

Figure 1:
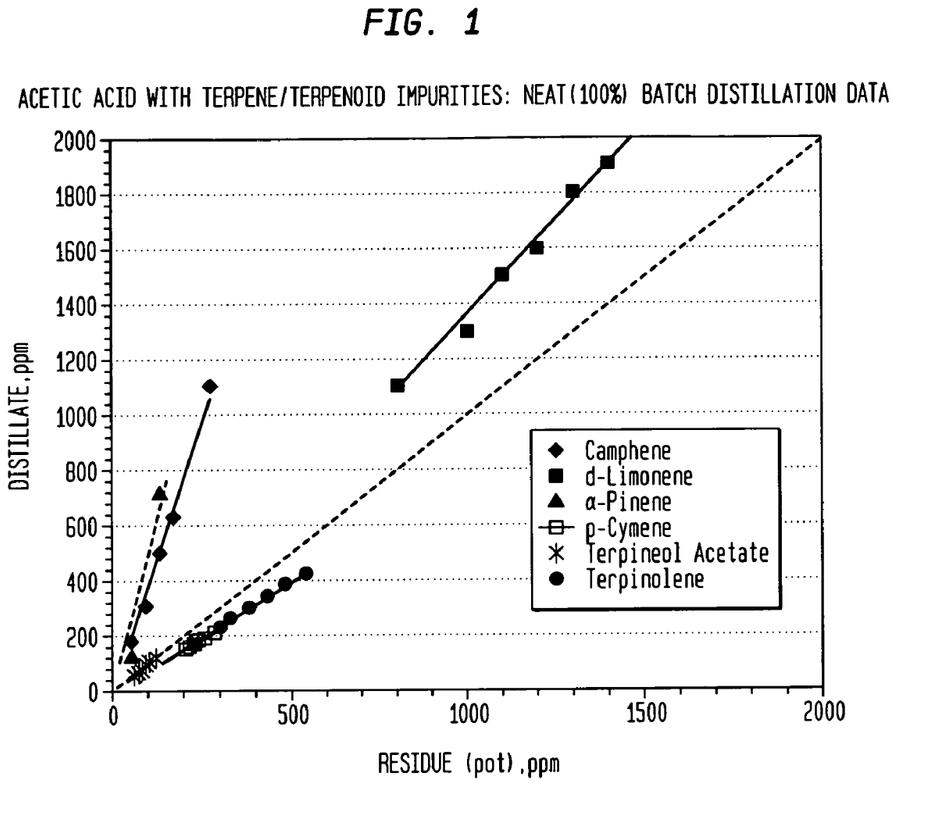
FIG. 1 is a plot of terpene and terpenoid concentrations in distillate and residue for dry acetic acid.

FIG. 1 illustrates the difficulty of removal of some impurities by distillation of neat (dry) acetic acid in batch distillation tests. Minimal separation of terpinolene, p-cymene, and terpineol acetate occurs as shown in FIG. 1. The camphene, limonene and c-pinene data show some enrichment in the distillate (vapor) versus residue (liquid) compositions.

Figure 2:
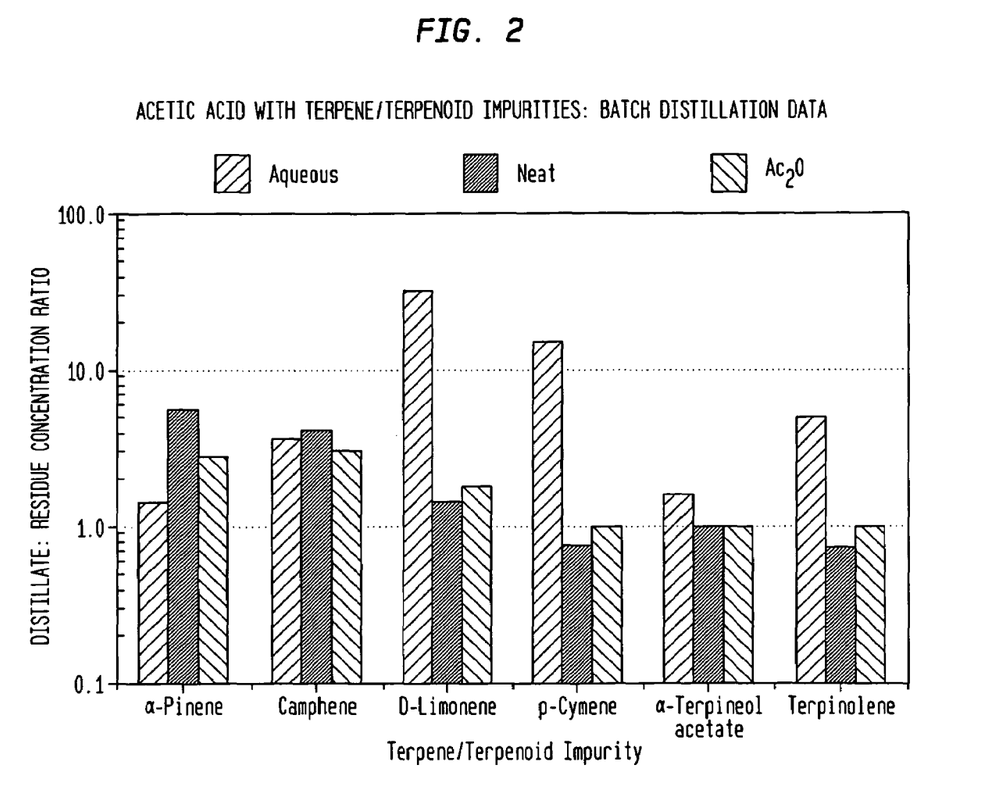
FIG. 2 is a graph of acetic acid batch distillation terpene and terpenoid removal results.

In the same investigation, it was found that removal could be unexpectedly and greatly enhanced by distillation with the addition of water, as shown in FIG. 2. Without intending to be bound to any particular theory, these results appear to confirm that the presence of water in a distillation tower helps enhance the removal of terpene/terpenoid impurities from acetic acid. We believe that limonenes and terpinolene, the largest impurities present in acetic acid recovered from a wood acetylation process, readily form azeotropes with water. These impurities exhibit enhanced removal via the overhead distillate stream due to the presence of low boiling-point water azeotropes with these impurities.

Batch Distillation Examples

Batch distillation experiments using recovered acetic acid, recovered acetic acid plus water, and recovered acetic acid plus acetic anhydride were conducted. The ratio of distillate-to-residue terpene/terpenoid impurity concentrations obtained from the batch distillation experiments (aqueous=70% recovered acetic acid/30% water, neat=100% recovered acetic acid, acetic anhydride=15% recovered acetic acid/85% acetic anhydride) are shown in FIG. 2. The data described in FIG. 2 for distillation of neat acid and for acetic acid and water are provided in Tables 1 and 2, below.

product stream is dramatically reduced (95%) when water is added to the distillation tower in amounts as low as 8% of acid feed rate by weight.

TABLE 3

Results of Simulated Acetic Acid Purification

| Run # | Units | A | B |
|---|---|---|---|
| Total Trays | | 65 | 65 |
| H2O Feed Tray | | — | 65 |
| Feed Tray | | 30 | 30 |
| Sidestream Tray | | — | — |
| Acetic Acid Feed Rate | g/hour | 0.98 | 0.98 |
| H2O Feed Rate | g/hour | 0 | 0.09 |
| Reflux/Distillate | ratio | 15 | 15 |

TABLE 1

Batch Distillation Results for Neat Recovered Acetic Acid with Terpene/Terpenoid and "Light-end" Impurities

| NEAT HOAc w/Terpenes | Feed | Residue (Pot) Samples, ppm (w/w) | | | | | | | Distillate Samples, ppm (w/w) | | | | | | |
|---|---|---|---|---|---|---|---|---|---|---|---|---|---|---|---|
| | | 1 | 2 | 3 | 4 | 5 | 6 | 7 | 1 | 2 | 3 | 4 | 5 | 6 | 7 |
| Total Light-Ends | <960 | <850 | <520 | <380 | <300 | <300 | <300 | <300 | 11120 | <3710 | <2250 | <680 | <310 | <330 | <300 |
| α-Pinene | 220 | 130 | <50 | <50 | <50 | <50 | <50 | <50 | 720 | 130 | <50 | <50 | <50 | <50 | <50 |
| Camphene | 200 | 270 | 170 | 130 | 90 | <50 | <50 | <50 | 1100 | 630 | 500 | 310 | 180 | 90 | <50 |
| D-Limonene | 1400 | 1700 | 1400 | 1300 | 1200 | 1100 | 1000 | 800 | 2400 | 1900 | 1800 | 1600 | 1500 | 1300 | 1100 |
| p-Cymene | 120 | 240 | 200 | 210 | 230 | 240 | 260 | 280 | 180 | 160 | 160 | 170 | 190 | 190 | 210 |
| α-Terpineol acetate | 60 | 60 | 70 | 80 | 90 | 100 | 120 | 120 | 60 | 70 | 80 | 100 | 110 | 120 | 120 |
| Terpinolene | 270 | 230 | 300 | 330 | 380 | 430 | 480 | 540 | 170 | 230 | 260 | 300 | 340 | 380 | 420 |
| Acetic Acid, wt % | 99.4 | 99.5 | 99.6 | 99.6 | 99.6 | 99.6 | 99.6 | 99.5 | 98.3 | 99.2 | 99.4 | 99.6 | 99.7 | 99.7 | 99.8 |

*Detectable limit for "light-ends" and terpene/terpenoid impurities <50 ppm

TABLE 2

Batch Distillation Results for Recovered Acetic Acid with Terpene/Terpenoid and "Light-end" Impurities Plus Water (70/30)

| 70% HOAc w/Terpenes + 30% Water | Residue (Pot) Samples, ppm (w/w) | | | | | | | Distillate Samples, ppm (w/w) | | | | | | |
|---|---|---|---|---|---|---|---|---|---|---|---|---|---|---|
| | 1 | 2 | 3 | 4 | 5 | 6 | 7 | 1 | 2 | 3 | 4 | 5 | 6 | 7 |
| Total Light-Ends | <680 | <300 | <300 | <300 | <300 | <300 | <300 | 9130 | <1670 | <410 | <300 | <300 | <300 | <300 |
| α-Pinene | <50 | <50 | <50 | <50 | <50 | <50 | <50 | 60 | 70 | 50 | <50 | <50 | <50 | <50 |
| Camphene | 80 | <50 | <50 | <50 | <50 | <50 | <50 | 140 | 180 | 130 | <50 | <50 | <50 | <50 |
| D-Limanene | 760 | <50 | <50 | <50 | <50 | <50 | <50 | 1600 | 1600 | 1000 | 370 | 280 | 210 | 200 |
| p-Cymene | 100 | <50 | <50 | <50 | <50 | <50 | <50 | 600 | 760 | 300 | 100 | 70 | 60 | <50 |
| β-Terpineol acetate | 50 | <50 | <50 | <50 | <50 | <50 | <50 | 90 | 80 | 60 | 60 | 50 | <50 | <50 |
| Terpinolene | 90 | <50 | <50 | <50 | <50 | <50 | <50 | 320 | 250 | 200 | 180 | 130 | 100 | 100 |
| Acetic Acid, wt % | 69.8 | 75.3 | 73.7 | 76.5 | 79.2 | 83 | 86.5 | 53.8 | 53 | 55.7 | 60.2 | 63.4 | 68.2 | 75.1 |
| Water, wt % | 30 | 24.6 | 26.3 | 23.5 | 20.8 | 17.0 | 13.5 | 44.8 | 46.4 | 44.0 | 39.7 | 36.5 | 31.7 | 24.9 |

*Detectable limit for "light-ends" and terpene/terpenoid impurities <50 ppm

The distillation results after adding water are especially pronounced for limonene and p-cymene (ratios greater than 10) and terpinolene (ratio greater than 3). In comparison, the distillation results of neat acetic acid for these impurities provided ratios below or just above 1. The results with acetic anhydride added before distillation are similar to the results of the neat acetic acid distillation.

Using a computer-simulated analysis, the data shown in Table 3 was generated. The results of Table 3 show that the total terpene and terpenoid impurities found in a residue TABLE 3-continued Results of Simulated Acetic Acid Purification

| Run # | Units | A | B |
|---|---|---|---|
| Sidestream Rate | g/hour | 0 | 0 |
| Overhead Rate | g/hour | 0.0054 | 0.09 |
| Residue Rate | g/hour | 0.975 | 0.975 |
| Feed Total Terpenoids | ppm | 452 | 452 |
| Residue Total Terpenoids | ppm | 371 | 20 |
| Residue Water | ppm | — | 0.03 |

TABLE 3-continued

Results of Simulated Acetic Acid Purification

| Run # | Units | A | B |
|---|---|---|---|
| Residue Acetic Acid | wt % | 99.87 | 100.00 |
| Overhead Acid | wt % | 85.71 | 4.80 |

Figure 3:
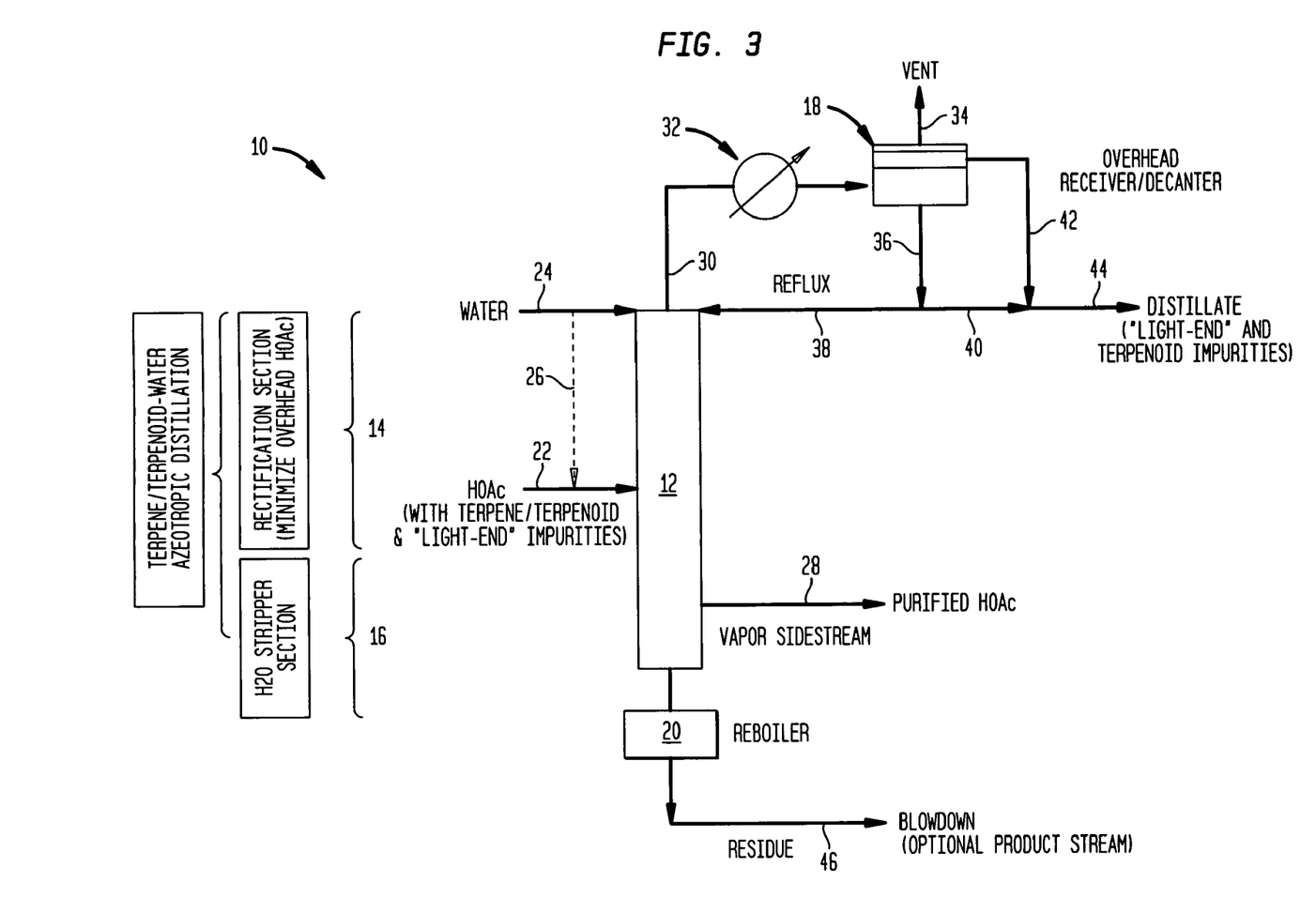
FIG. 3 is a schematic diagram of one embodiment of the invention.

A continuous method of removing terpenoids from the recovered acid is shown in FIG. 3. Apparatus 10 for purifying acetic acid consists of a distillation tower 12 having a rectification section 14 and a water stripper section 16, an overhead receiver/decanter 18, and a reboiler 20.

Recovered acetic acid containing terpene and terpenoid impurities is fed to the distillation tower 12 via line 22 at about the middle of the tower. Water is also fed to the distillation tower via line 24 at the top of the tower. Water can also be introduced with the recovered acetic acid via line 26. Purified acetic acid is removed from the distillation tower at the sidestream line 28 as vapor or liquid, preferentially vapor. However, the purified acetic acid product could be withdrawn as bottoms rather than as a sidestream. Overheads are removed from the tower via line 30, passed through condenser 32, and fed to overhead receiver/decanter 18.

The reboiler 20 heats bottoms from the distillation tower 12. Residue is drawn off via line 46 as blowdown, providing an optional product stream.

The overhead receiver/decanter 18 decants a distillate containing light-end and terpene and terpenoid impurities from the condensed overheads, which can be removed from the receiver/decanter via line 42. Non-condensed gases are vented via line 34. The remaining liquid condensate is either refluxed to the distillation tower via line 38 or discharged with the distillate via line 40.

Particular examples are described below.

Continuous Fractional Distillation Examples

Several experiments were run using continuous fractional distillation towers of the class generally described above under different conditions. The procedures and results are summarized below and in Table 4.

Examples 1-5

The first series of lab distillation experiments were conducted in a 45-tray tower using the following parameters. A mixture of acetic acid and water was fed at tray-20. The acid carry-over during these initial experiments averaged ~0.31 wt %. The product stream contained about 10.7% water, and the distillate contained <1% acetic acid. Other factors used in this series of experiments are shown below.

Water feed rate=0.1×acid feed rate $D/F$=0.07

$R/D$~=15:1

Examples 6-9

A second series of lab distillation experiments were made with only acetic acid fed to tray-20 and the water fed at the top of the 45-tray column. This change in the water addition point was made to determine any measurable effects on the amount of acid carry-over, which would be a potential acetic acid efficiency loss. All subsequent experiments were made using a water addition point at the top tray of the acetic acid distillation tower. Acid carry-over was reduced to typically <0.2 wt % when using the water addition point at the top tray (see Table 4, below).

Examples 10-14

An additional 10 trays were added to the tower for the third series of experiments, the acetic acid feed tray was moved to tray-25, and water addition to the top tray was continued. This new tower configuration increased the number of trays between the feed and sidestream product locations, and between the feed tray and the tower overhead, by 5 trays, respectively.

Experiments 10-14 demonstrated that acetic acid could be purified to more closely approach glacial acetic acid specification limits (listed above) for assay and water, averaging an assay value of about 99.9% and a water content of 0.025 wt %. However, the average color was about 5.3 and permanganate time averaged less than 90 minutes, which did not meet the 2 hour minimum specification. Permanganate time was the key specification limit not achieved by this series of experiments. The total terpene and terpenoid impurities were attenuated from an average acetic acid feed concentration of ~410 ppm down to ~30 ppm (average) in the sidestream product. Also, "light-end" impurities totaling ~700 ppm in the acetic acid feed were essentially completely removed from the sidestream product.

The sidestream water concentration was found to be inversely proportional to the amount of terpenoid impurities measured in the sidestream product (see Table 4.

Examples 1-9 produced a sidestream product that contained detectable (ppm) levels of terpene/terpenoid impurities, and high water concentrations (>2 wt % water). However, these experiments met the 2 hour minimum permanganate time specification.

Water added to the acetic acid purification tower, for improved terpenoid impurity removal, generates the largest impurity that needs to be removed to meet glacial acetic acid specifications. The water concentration in the product stream is directly related to temperature and, therefore, pressure compensated temperature measurement can be used for process control of the product stream assay.

Figure 4:
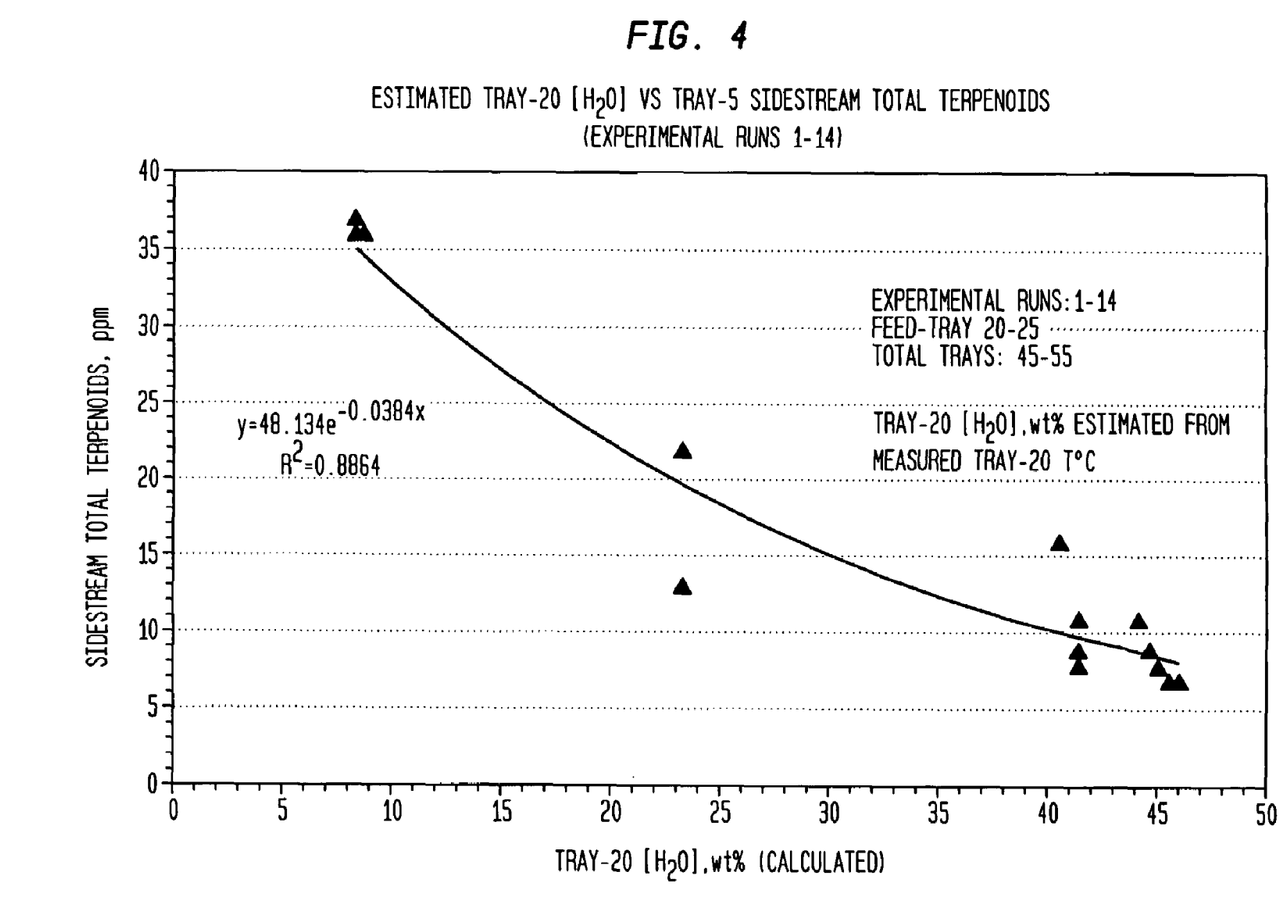
FIG. 4 is a plot of water concentration vs. terpenes and terpenoids in a purified product stream.

The total terpenoids concentration below the feed tray of the tower is a function of the concentration of water present below the feed tray of the tower. The estimated tray-20 water concentration versus sidestream product total terpenoid data are shown in FIG. 4. This figure shows the relationship between impurity content of a product taken near the bottom of the distillation column versus the amount of water in the distillation column at or below the feed location.

The amount of water fed to the purification tower experiments varied from ~5% to 20% (w/w) based on the acetic acid feed rate. Increased water addition rates resulted in increased distillate rates and, in general, increased the water concentration below the feed tray of the tower. The original tower configuration with 45 trays did not demonstrate the capability to achieve specification-grade water concentrations in the sidestream product stream even when the water addition rate was reduced to ~8%. Increasing the number of trays between the feed and sidestream product (from 15 to 20 trays) and increasing the total number of trays to 55 provided sufficient rectification for achieving low sidestream water concentrations and for maintaining low acetic acid carry-over. By increasing the number of trays between the feed and sidestream points, the water profile could be lowered for improved terpenoid removal, and the water could be adequately stripped from the acetic acid before reaching the tray-5 sidestream.

The acid carry-over was very low for all of the runs using water addition to the top tray, and resulted in acetic acid losses cation. However, the water concentration was too high (i.e., ~0.75 wt %).

Note in Table 4 that almost no acetic acid was found in the overhead (i.e., less than 0.36%). Therefore, it appears that the overhead is essentially all water.

TABLE 4

Acetic Acid Purification Tower Experiments

| Parameter/Run# | Units | 1 | 2 | 3 | 4 | 5 | 6 | 7 | 8 | 9 | 10 | 11 | 12 | 13 | 14 | 15 | 16 | 17 |
|---|---|---|---|---|---|---|---|---|---|---|---|---|---|---|---|---|---|---|
| Total Trays | | 45 | 45 | 45 | 45 | 45 | 45 | 45 | 45 | 45 | 55 | 55 | 55 | 55 | 55 | 60 | 60 | 60 |
| H2O Feed Tray | | 20 | 20 | 20 | 20 | 20 | 45 | 45 | 45 | 45 | 55 | 55 | 55 | 55 | 55 | 60 | 60 | 60 |
| Feed Tray | | 20 | 20 | 20 | 20 | 20 | 20 | 20 | 20 | 20 | 25 | 25 | 25 | 25 | 25 | 35 | 35 | 35 |
| Vapor Sidestream Tray | | 5 | 5 | 5 | 5 | 5 | 5 | 5 | 5 | 5 | 5 | 5 | 5 | 5 | 5 | 5 | 5 | 5 |
| Acetic Acid Feed Rate | g/hour | 239.5 | 235.6 | 248.2 | 274.8 | 272.5 | 301.4 | 281.3 | 301.4 | 263.75 | 288 | 282.4 | 311.4 | 311.4 | 302.9 | 288.4 | 300 | 300 |
| H2O Feed Rate | g/hour | 59.1 | 60 | 62.1 | 32.9 | 29.61 | 26 | 26 | 27.9 | 24.4 | 14.93 | 14 | 15 | 25.7 | 20 | 30 | 30 | 30 |
| Reflux/Distillate | ratio | 15 | 15 | 15 | 15 | 15 | 15 | 15 | 15 | 15 | 16 | 20 | 18 | 15 | 15 | 14 | 14 | 14 |
| Sidestream Rate | g/hour | 248.3 | 266.7 | 295.7 | 269.4 | 294.4 | 301.4 | 281.3 | 301.4 | 263.75 | 288 | 280.7 | 301.43 | 294.3 | 288.6 | 269.1 | 300 | 300 |
| Overhead Rate | g/hour | 14.3 | 19.5 | 26.5 | 18.5 | 19.3 | 21.6 | 20.1 | 21.6 | 18.88 | 14 | 15.1 | 14.3 | 18.1 | 17.1 | 22.8 | 28.9 | 15 |
| Residue Rate | g/hour | 8.3 | 10 | 10.5 | 9.2 | 9.71 | 8.56 | 8 | 8.57 | 7.5 | 6.67 | 6.67 | 7.14 | 7.14 | 7.14 | 4.4 | 4.4 | 5 |
| Feed Total Terpenoids | ppm | 363 | 371 | 365 | 411 | 399 | 457 | 453 | 451 | 446 | 456 | 470 | 438 | 405 | 457 | 431 | 391 | 447 |
| Tray-20 Temperature | °C. | 102.5 | 102.3 | 102.4 | 103.3 | 103.3 | 103.5 | 103.3 | 102.6 | 102.7 | 113.6 | 113.8 | 113.8 | 108 | 108 | 104.1 | 104.2 | 103.8 |
| Tray-20 Water (estimated) | wt % | 45.1 | 46.1 | 45.6 | 41.5 | 41.5 | 40.6 | 41.5 | 44.7 | 44.2 | 8.7 | 8.3 | 8.3 | 23.3 | 23.3 | 38.0 | 37.6 | 39.3 |
| Sidestream Total Terpenoids | ppm | 8 | 7 | 7 | 8 | 9 | 16 | 11 | 9 | 11 | 36 | 36 | 37 | 22 | 13 | 0.5 | 1 | 1 |
| Sidestream Water | wt % | 21.3 | 14 | 11.9 | 3.1 | 3.1 | 3.8 | 1.8 | 2.57 | 2 | 0.033 | 0.012 | 0.017 | 0.034 | 0.026 | 2 | 0.66 | 0.83 |
| Sidestream Acetic Acid | wt % | 78.70 | 85.50 | 87.90 | 96.30 | 96.70 | 96.20 | 98.20 | 97.43 | 98.00 | 99.96 | 99.98 | 99.98 | 99.96 | 99.97 | 98.00 | 99.34 | 99.17 |
| Sidestream KMnO4 Time | minutes | >180 | >180 | >180 | >180 | >180 | NA | NA | >180 | >180 | <90 | <90 | <90 | <90 | <90 | >30 | >180 | >180 |
| Overhead Acid | wt % | 0.23 | 0.29 | 0.34 | 0.33 | 0.36 | 0.2 | 0.19 | 0.13 | 0.14 | 0.04 | 0.05 | 0.04 | 0.04 | 0.03 | 0.17 | 0.22 | 0.23 | of <0.01% (w/w based on the amount of acetic acid fed to the column). Therefore, the feed point could possibly be raised while maintaining acceptably low overhead acid losses (e.g., acetic acid feed at tray-30 for a 55-tray tower, or the 30 trays between the feed and overhead could be maintained using a 60 tray tower with a tray-30 feed location).

Examples 15-17

The distillation column was re-configured with 60 total trays, with feed at tray-30 and water addition to the top tray. The sidestream location was maintained at tray-5. Four initial distillation runs were made using the new 60-tray acetic acid purification column configuration with an additional 5 trays between the feed and sidestream locations. The purpose of increasing the number of trays in this portion of the distillation tower was to increase the contact of the azeotroping agent (i.e., water) with the terpene/terpenoid impurities present in the acetic acid feed, while providing a sufficient number of trays to lower the sidestream product water concentration.

Runs 15-17 resulted in ≦1 ppm levels of terpene/terpenoid impurities in the sidestream product. The permanganate time was >180 minutes for runs 16 and 17, which met the specifi- While the invention has been described in connection with purifying acetic acid in connection with particular Examples, modifications within the spirit and scope of the present invention, set forth in the appended claims, will be readily apparent to those of skill in the art.

What is claimed is:

1. A method of purifying acetic acid containing terpene and terpenoid impurities, comprising:
   (a) supplying acetic acid containing terpene or terpenoid impurities and water to a distillation column;
   (b) azeotropically removing terpene or terpenoid impurities as low boiling point water azeotropes in distillate from the mixture of acetic acid and water supplied to the column; and
   (c) withdrawing a product stream from the column comprising acetic acid purified of terpene or terpenoid impurities.

2. The method of purifying acetic acid containing terpene and terpenoid impurities according to claim 1, wherein the product stream withdrawn from the column is a liquid.

3. The method of purifying acetic acid containing terpene and terpenoid impurities according to claim 2, further comprising drying the liquid product stream.

4. The method of purifying acetic acid containing terpene and terpenoid impurities according to claim 1, wherein the acetic acid:water feed ratio is at least 2:1 and up to 50:1.

5. The method of purifying acetic acid containing terpene and terpenoid impurities according to claim 1, wherein the acetic acid:water feed ratio is at least 4:1.

6. The method of purifying acetic acid containing terpene and terpenoid impurities according to claim 1, wherein the acetic acid:water feed ratio is at least 7:1 and up to about 15:1.

7. The method of purifying acetic acid containing terpene and terpenoid impurities according to claim 1, wherein the method provides removal of 70% by weight or more of the total terpene and terpenoid impurities.

8. The method of purifying acetic acid containing terpene and terpenoid impurities according to claim 1, wherein the method provides removal of 80% by weight or more of the total terpene and terpenoid impurities.

9. The method of purifying acetic acid containing terpene and terpenoid impurities according to claim 1, wherein the method provides removal of 85% by weight or more of the total terpene and terpenoid impurities.

10. The method of purifying acetic acid containing terpene and terpenoid impurities according to claim 1, wherein the amount of water in the product stream is 25% or less.

11. The method of purifying acetic acid containing terpene and terpenoid impurities according to claim 1, wherein the amount of water in the product stream is 15% or less.

12. The method of purifying acetic acid containing terpene and terpenoid impurities according to claim 1, wherein the amount of water in the product stream is 5% or less.

13. The method of purifying acetic acid containing terpene and terpenoid impurities according to claim 1, wherein the amount of water in the product stream is 2% or less.

14. The method of purifying acetic acid containing terpene and terpenoid impurities according to claim 1, wherein the amount of water in the product stream is 1% or less.

15. The method of purifying acetic acid containing terpene and terpenoid impurities according to claim 1, wherein the amount of water in the product stream is 0.2% or less.

16. The method of purifying acetic acid containing terpene and terpenoid impurities according to claim 1, effective to remove at least 80% of one or more of the following: terpinenes; terpinolenes; α-terpineol acetate; pinenes; α-fenchene; camphene; p-methyl isopropyl benzene (p-cymene); limonenes; α-fenchyl acetate; isobornyl acetate; and mixtures thereof.

17. A method of purifying acetic acid containing terpene and terpenoid impurities, comprising:
(a) recovering dry acetic acid from a wood acetylation process;
(b) supplying the acetic acid and water to a distillation column;
(c) azeotropically removing terpene or terpenoid impurities as low boiling point water azeotropes in distillate from the mixture of acetic acid and water supplied to the column;
(d) withdrawing a product stream from the column comprising acetic acid purified of terpene or terpenoid impurities; and
(e) drying the product stream.

18. The method of purifying acetic acid containing terpene and terpenoid impurities according to claim 17, wherein the method further comprises maintaining a water concentration in the tower above a point at which the product stream is withdrawn of at least 10%.

19. The method of purifying acetic acid containing terpene and terpenoid impurities according to claim 17, wherein the method further comprises maintaining a water concentration in the tower above a point at which the product stream is withdrawn of at least 20%.

20. The method of purifying acetic acid containing terpene and terpenoid impurities according to claim 17, wherein the method further comprises maintaining a water concentration in the tower above a point at which the product stream is withdrawn of at least 30%.

21. The method of purifying acetic acid containing terpene and terpenoid impurities according to claim 17, wherein the method further comprises maintaining a water concentration in the tower above a point at which the product stream is withdrawn of at least 40%.

22. A method of purifying acetic acid containing terpene and terpenoid impurities, comprising:
(a) supplying acetic acid containing terpene or terpenoid impurities to a distillation column;
(b) feeding water to the distillation column at a location above the location where acetic acid is supplied;
(c) azeotropically removing terpene or terpenoid impurities as low boiling point water azeotropes in distillate from the mixture of acetic acid and water supplied to the column by way of withdrawing overhead vapor from the distillation column;
(d) condensing the overhead vapor;
(e) refluxing a portion of the condensed distillate withdrawn from the distillation column; and
(f) withdrawing a product stream from the column comprising acetic acid purified of terpene or terpenoid impurities.

23. The method of purifying acetic acid containing terpene and terpenoid impurities according to claim 22, wherein the water feed:distillate ratio is not higher than 5:1.

24. The method of purifying acetic acid containing terpene and terpenoid impurities according to claim 22, wherein the water feed:distillate ratio is not more than 2:1.

25. The method of purifying acetic acid containing terpene and terpenoid impurities according to claim 22, wherein the water feed:distillate ratio is at least 1:1 and not more than 2:1.

26. The method of purifying acetic acid containing terpene and terpenoid impurities according to claim 22, wherein the reflux:distillate ratio is at least 1:1.

27. The method of purifying acetic acid containing terpene and terpenoid impurities according to claim 22, wherein the reflux:distillate ratio is at least 3:1.

28. The method of purifying acetic acid containing terpene and terpenoid impurities according to claim 22, wherein the reflux:distillate ratio is at least 10:1.

29. The method of purifying acetic acid containing terpene and terpenoid impurities according to claim 22, wherein the reflux:distillate ratio is at least 10:1 and not more than 25:1.

* * * * *